United States Patent
Wang et al.

(10) Patent No.: US 9,499,747 B2
(45) Date of Patent: Nov. 22, 2016

(54) METHOD AND REACTOR FOR CRACKING HYDROCARBON

(75) Inventors: Shizhong Wang, Shanghai (CN); Wenqing Peng, Shanghai (CN); Qijia Fu, Shanghai (CN); Zhigang Deng, Shanghai (CN); Zhaoping Wu, Shanghai (CN); Chuan Lin, Shanghai (CN); Yanfei Gu, Shanghai (CN); Xiao Zhang, Shanghai (CN); Lawrence Bernard Kool, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 271 days.

(21) Appl. No.: 13/115,610

(22) Filed: May 25, 2011

(65) Prior Publication Data

US 2011/0295051 A1    Dec. 1, 2011

(30) Foreign Application Priority Data

May 31, 2010   (CN) .......................... 2010 1 0192512

(51) Int. Cl.
C07C 4/02       (2006.01)
C07C 4/06       (2006.01)
(Continued)

(52) U.S. Cl.
CPC ............ *C10G 9/203* (2013.01); *B01J 19/0026* (2013.01); *B01J 19/02* (2013.01); *B01J 19/2425* (2013.01);
(Continued)

(58) Field of Classification Search
USPC ........................................................ 585/752
See application file for complete search history.

(56) References Cited

U.S. PATENT DOCUMENTS 3,718,553 A * 2/1973 Stover ...................... 208/120.15
4,208,269 A * 6/1980 Gladrow et al. ........... 208/120.1
(Continued)

FOREIGN PATENT DOCUMENTS

CN         1408637 A      4/2003
CN       101069844 A     11/2007
(Continued)

OTHER PUBLICATIONS

Woerde, H.M., et al. "Mitigate coke formation." From Hydrocarbon Processing, Petrochemical Developments, Mar. 2002.
(Continued)

*Primary Examiner* — In Suk Bullock
*Assistant Examiner* — Youngsul Jeong
(74) *Attorney, Agent, or Firm* — Wegman, Hessler & Vanderburg

(57) ABSTRACT

A method for cracking hydrocarbon, comprises: providing steam and hydrocarbon; and feeding steam and hydrocarbon into a reactor accessible to hydrocarbon and comprising a perovskite material of formula $A_aB_bC_cD_dO_{3-\delta}$, wherein $0<a<1.2$, $0\leq b\leq 1.2$, $0.9<a+b\leq 1.2$, $0<c<1.2$, $0\leq d\leq 1.2$, $0.9<c+d\leq 1.2$, $-0.5<\delta<0.5$; A is selected from calcium, strontium, barium, and any combination thereof; B is selected from lithium, sodium, potassium, rubidium and any combination thereof; C is selected from cerium, zirconium, antimony, praseodymium, titanium, chromium, manganese, ferrum, cobalt, nickel, gallium, tin, terbium and any combination thereof; and D is selected from lanthanum, cerium, praseodymium, neodymium, promethium, samarium, europium, gadolinium, terbium, dysprosium, holmium, ebium, thulium, ytterbium, lutetium, scandium, titanium, vanadium, chromium, manganese, ferrum, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, gallium, indium, tin, antimony and any combination thereof.

9 Claims, 2 Drawing Sheets

Figure 1:
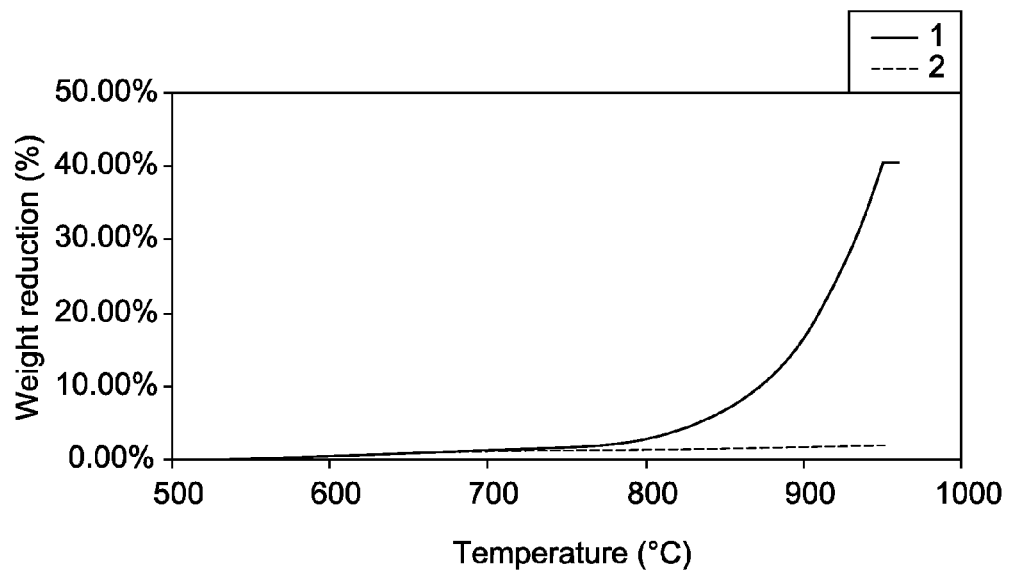

(51) Int. Cl.
| | |
|---|---|
| *C07C 5/32* | (2006.01) |
| *C10G 71/00* | (2006.01) |
| *C10G 9/20* | (2006.01) |
| *B01J 19/00* | (2006.01) |
| *B01J 19/02* | (2006.01) |
| *B01J 19/24* | (2006.01) |
| *C10G 9/18* | (2006.01) |
| *B01J 23/00* | (2006.01) |

(52) U.S. Cl.
CPC ............ *C10G 9/18* (2013.01); *B01J 23/002* (2013.01); *B01J 2219/0218* (2013.01); *B01J 2219/0263* (2013.01); *B01J 2219/0286* (2013.01); *C10G 2300/107* (2013.01); *C10G 2300/1033* (2013.01); *C10G 2300/1044* (2013.01); *C10G 2300/1059* (2013.01); *C10G 2300/1077* (2013.01); *C10G 2300/1081* (2013.01); *C10G 2300/807* (2013.01); *C10G 2400/20* (2013.01)

(56) References Cited

U.S. PATENT DOCUMENTS

| | | | |
|---|---|---|---|
| 4,404,087 | A | 9/1983 | Reed et al. |
| 4,411,772 | A | 10/1983 | Schucker et al. |
| 4,412,911 | A | 11/1983 | Schucker et al. |
| 4,418,008 | A | 11/1983 | Schucker et al. |
| 4,446,011 | A | 5/1984 | Wheelock et al. |
| 4,454,021 | A | 6/1984 | Watanabe et al. |
| 4,552,643 | A | 11/1985 | Porter et al. |
| 4,666,583 | A | 5/1987 | Porter et al. |
| 4,687,567 | A | 8/1987 | Porter et al. |
| 4,692,234 | A | 9/1987 | Porter et al. |
| 5,000,836 | A | 3/1991 | Forester |
| 5,015,358 | A | 5/1991 | Reed et al. |
| 5,198,596 | A | 3/1993 | Kaminsky et al. |
| 6,228,253 | B1 | 5/2001 | Gandman |
| 6,475,647 | B1 | 11/2002 | Mendez et al. |
| 6,585,883 | B1 | 7/2003 | Kelemen et al. |
| 6,657,022 | B2 | 12/2003 | Williams et al. |
| 7,625,653 | B2 | 12/2009 | Kuroha et al. |
| 2002/0187091 | A1 | 12/2002 | Deevi | |
| 2003/0070963 | A1* | 4/2003 | Zimmermann et al. | 208/106 |
| 2004/0152586 | A1 | 8/2004 | Ou et al. | |
| 2004/0188323 | A1 | 9/2004 | Tzatzov et al. | |
| 2006/0135838 | A1* | 6/2006 | Bagherzadeh et al. | 585/660 |
| 2008/0184915 | A1 | 8/2008 | Tonkovich et al. | |
| 2010/0112408 | A1* | 5/2010 | Yang et al. | 429/33 |

FOREIGN PATENT DOCUMENTS

| | | |
|---|---|---|
| EP | 2154225 A1 * | 2/2010 |
| WO | WO 93/13037 A1 | 7/1993 |
| WO | 2001023169 A1 | 4/2001 |

OTHER PUBLICATIONS

Yang, et al. "Enhanced Sulfur and Coking Tolerance of a Mixed Ion Conductor for SOFCs: BaZr0.1Ce0.7Y0.2-xYbxO3- . . . " Science, vol. 326, Oct. 2, 2009.

Search Report and Written Opinion from corresponding EP Application No. 11167508.8-1270 dated Jul. 12, 2012.

Urasaki, K. et al., "Catalytic activities and coking resistance of Ni/perovskites in steam reforming of methane", vol. 286, No. 1, pp. 23-29, May 26, 2005.

Communication Pursuant to Article 94(3) EPC issued by the European Patent Office mailed Jan. 31, 2014 for European Application No. 11 167 508.8.

Unofficial English Translation of Chinese Office Action issued in connection with corresponding CN Application No. 201010192512.4 on Apr. 28, 2013.

Unofficial English Translation of Chinese Office Action issued in connection with corresponding CN Application No. 201010192512.4 on Jan. 24, 2014.

European Office Action issued in connection with corresponding EP Application No. 11167508.8 on Jan. 31, 2014.

Office Action mailed Sep. 4, 2014 in Chinese Patent Application No. 2010101925124 filed May 31, 2010.

Chen Xingyong et al., "Basic Organic Chemical Industry Production and Process", Chemical Industry Express, pp. 32-41, 2004.

English Translation of Search Report issued Aug. 27, 2014 by the State Intellectual Property Office.

* cited by examiner

METHOD AND REACTOR FOR CRACKING HYDROCARBON

BACKGROUND

The invention relates generally to methods and reactors for cracking hydrocarbon. More specifically, the invention relates to methods and reactors for cracking hydrocarbon, in which the build-up of coke deposits are undesirable.

In the petrochemical industry, hydrocarbons such as ethane, propane, butane and naphtha are cracked in reactors, in the presence of from about 30 to 70 weight percentage of steam, at temperatures of from about 700° C. to 870° C. in order to produce light olefins such as ethylene and propylene. Sometimes, hydrocarbons such as bottoms from atmospheric and vacuum distillation of crude oil are cracked in reactors at a temperature in a range from about 480° C. to about 600° C. in the presence of about 1 wt % to about 2 wt % steam.

During hydrocarbon cracking processes, the build-up of carbonaceous deposits (i.e. coke deposits) usually happens on inner surfaces of reactor components, for instance, inner radiant tube surfaces of furnace equipment. The inner radiant tube surfaces become gradually coated with a layer of coke which raises the radiant tube metal temperature (TMT) and increases the temperature drop through radiant coils. In addition, coke build-up adversely affects the physical characteristics of the reactor components, such as the radiant tubes, by deteriorating mechanical properties such as stress rupture, thermal fatigue, and ductility.

In order to decoke reactor components, the reactor must be periodically shut down. Typically, the decoking is carried out by combustion of the coke deposits with steam/air at temperatures of up to 1000° C. Such decoking operations are required approximately every 10 to 80 days, depending on the operation mode, types of hydrocarbons and hydrocarbons throughput, and result in production loss since hydrocarbons feeding must be stopped for such decoking operation.

A variety of methods have been considered in order to overcome the disadvantages of coke build-up on reactor components, such as furnace tube inner surfaces. These approaches include: metallurgy upgrade to alloys with increased chromium content of the metal substrates used in the furnaces; adding additives such as sulfur, dimethyl sulfide (DMS), dimethyl disulfide (DMDS) or hydrogen sulfide to the feedstock; increasing steam dilution of feedstock, and improved process control; selectively pre-treating the inner surface of the coils; inert surface coating; and catalytic gasification of coke to produce $CO/CO_2$ and hydrogen.

While some of the aforementioned methods and systems have general use in the petrochemical industry, it is desirable to provide a method and reactor that obviates and mitigates the shortcomings of the prior art and successfully reduces or eliminates the build-up of coke deposits.

BRIEF DESCRIPTION

In one aspect, the invention relates to a method for cracking hydrocarbon, comprising: providing steam and hydrocarbon; and feeding steam and hydrocarbon into a reactor having an inner surface accessible to hydrocarbon, the inner surface comprising a perovskite material of formula $A_aB_bC_cD_dO_{3-\delta}$, wherein $0<a<1.2$, $0=<b<=1.2$, $0.9<a+b\leq1.2$, $0<c<1.2$, $0\leq d\leq1.2$, $0.9<c+d\leq1.2$, $-0.5<\delta<0.5$; A is selected from calcium (Ca), strontium (Sr), barium (Ba), and any combination thereof; B is selected from lithium (Li), sodium (Na), potassium (K), rubidium (Rb) and any combination thereof; C is selected from cerium (Ce), zirconium (Zr), antimony (Sb), praseodymium (Pr), titanium (Ti), chromium (Cr), manganese (Mn), ferrum (Fe), cobalt (Co), nickel (Ni), gallium (Ga), tin (Sn), terbium (Tb) and any combination thereof; and D is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ebium (Er), thulium (Tm), ytterbium (Yb), lutetium (Lu), scandium (Sc), titanium (Ti), vanadium (V), chromium (Cr), manganese (Mn), ferrum (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), indium (In), tin (Sn), antimony (Sb) and any combination thereof.

In another aspect, the invention relates to a reactor for cracking hydrocarbon having an inner surface accessible to the hydrocarbon, the inner surface comprising a perovskite material of formula $A_aB_bC_cD_dO_{3-\delta}$, wherein $0<a<1.2$, $0\leq b\leq1.2$, $0.9<a+b\leq1.2$, $0<c<1.2$, $0\leq d\leq1.2$, $0.9<c+d\leq1.2$, $-0.5<\delta<0.5$; A is selected from calcium (Ca), strontium (Sr), barium (Ba), and any combination thereof; B is selected from lithium (Li), sodium (Na), potassium (K), rubidium (Rb), and any combination thereof; C is selected from cerium (Ce), zirconium (Zr), antimony (Sb), praseodymium (Pr), titanium (Ti), chromium (Cr), manganese (Mn), ferrum (Fe), cobalt (Co), nickel (Ni), gallium (Ga), tin (Sn), terbium (Tb) and any combination thereof; and D is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ebium (Er), thulium (Tm), ytterbium (Yb), lutetium (Lu), scandium (Sc), titanium (Ti), vanadium (V), chromium (Cr), manganese (Mn), ferrum (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), indium (In), tin (Sn), antimony (Sb) and any combination thereof.

DRAWINGS

Figure 2:
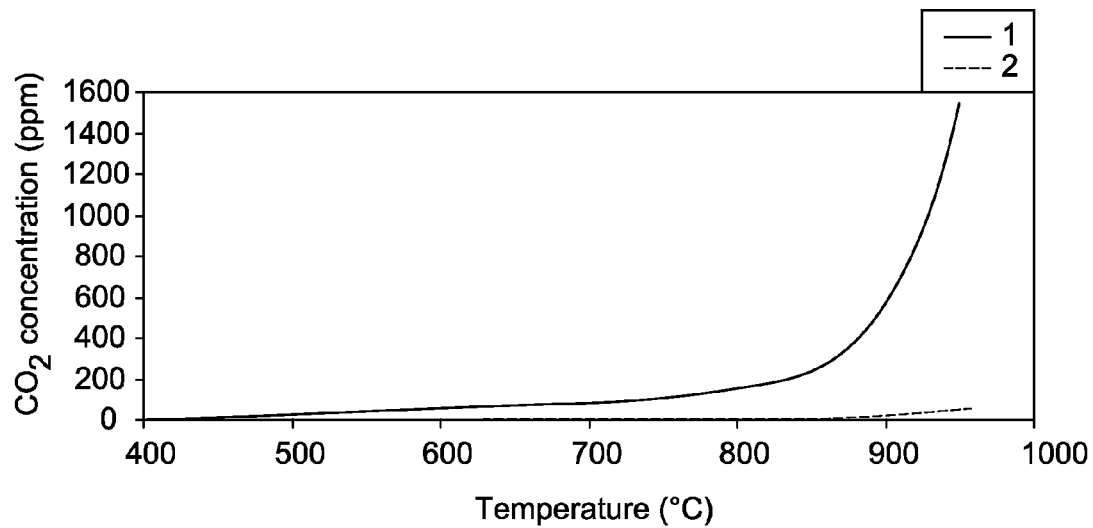
Figure 3:
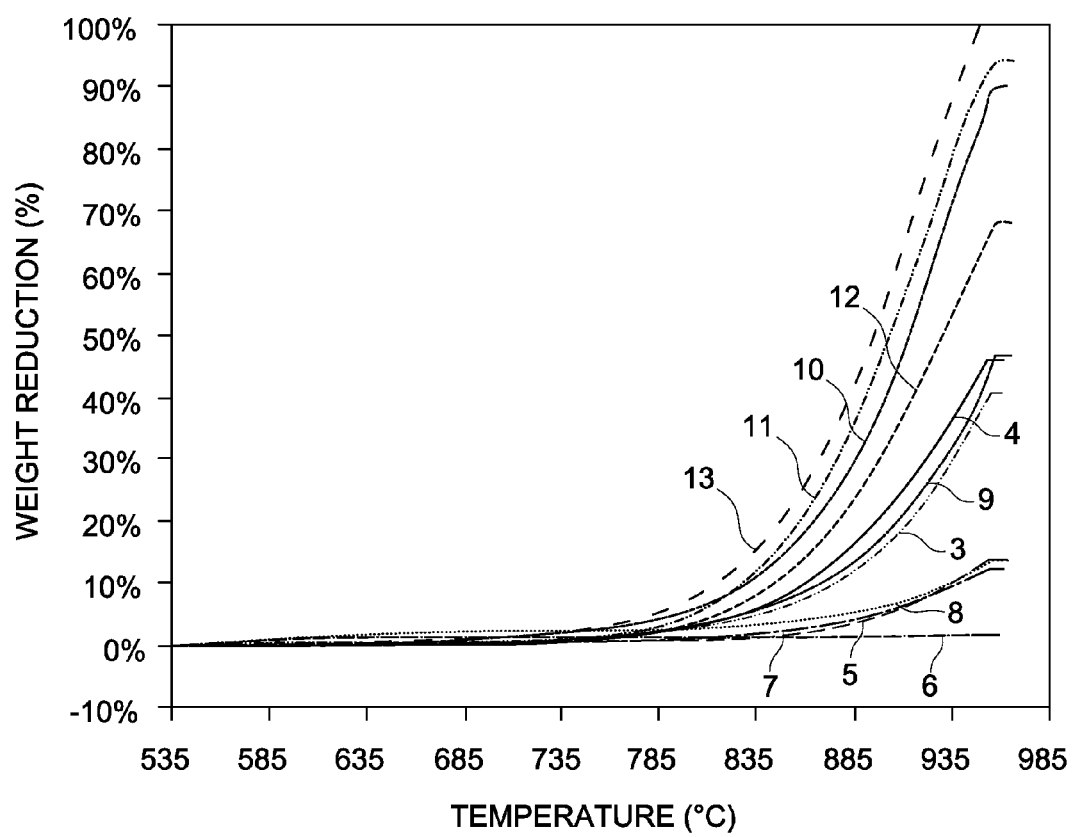

These and other features, aspects, and advantages of the present invention will become better understood when the following detailed description is read with reference to the accompanying drawings, wherein:

FIG. 1 shows the weight reduction percentages of the carbon black in the sample 1 and sample 2 after the sample 1 and the sample 2 were exposed to the helium-steam mixture compared with before exposure at different temperatures;

FIG. 2 shows the concentration of carbon dioxide generated after the sample 1 and the sample 2 were exposed to the helium-steam mixture at different temperatures; and FIG. 3 shows the weight reduction percentages of carbon black in samples 3-13 after the samples 3-13 were exposed to the helium-steam mixture with respect to before exposure at different temperatures.

DETAILED DESCRIPTION

In one aspect, the invention relates to a method for cracking hydrocarbon, comprising: providing steam and hydrocarbon; and feeding steam and hydrocarbon into a reactor having an inner surface accessible to hydrocarbon, the inner surface comprising a perovskite material of formula $A_aB_bC_cD_dO_{3-\delta}$, wherein $0<a<1.2$, $0\leq b\leq 1.2$, $0.9<a+b\leq 1.2$, $0<c<1.2$, $0\leq d\leq 1.2$, $0.9<c+d\leq 1.2$, $-0.5<\delta<0.5$; A is selected from calcium (Ca), strontium (Sr), barium (Ba), and any combination thereof; B is selected from lithium (Li), sodium (Na), potassium (K), rubidium (Rb) and any combination thereof; C is selected from cerium (Ce), zirconium (Zr), antimony (Sb), praseodymium (Pr), titanium (Ti), chromium (Cr), manganese (Mn), ferrum (Fe), cobalt (Co), nickel (Ni), gallium (Ga), tin (Sn), terbium (Tb) and any combination thereof; and D is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ebium (Er), thulium (Tm), ytterbium (Yb), lutetium (Lu), scandium (Sc), titanium (Ti), vanadium (V), chromium (Cr), manganese (Mn), ferrum (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), indium (In), tin (Sn), antimony (Sb) and any combination thereof.

In another aspect, the invention relates to a reactor for cracking hydrocarbon having an inner surface accessible to the hydrocarbon, the inner surface comprising a perovskite material of formula $A_aB_bC_cD_dO_{3-\delta}$, wherein $0<a<1.2$, $0\leq b\leq 1.2$, $0.9<a+b\leq 1.2$, $0<c<1.2$, $0\leq d\leq 1.2$, $0.9<c+d\leq 1.2$, $-0.5<\delta<0.5$; A is selected from calcium (Ca), strontium (Sr), barium (Ba), and any combination thereof; B is selected from lithium (Li), sodium (Na), potassium (K), rubidium (Rb), and any combination thereof; C is selected from cerium (Ce), zirconium (Zr), antimony (Sb), praseodymium (Pr), titanium (Ti), chromium (Cr), manganese (Mn), ferrum (Fe), cobalt (Co), nickel (Ni), gallium (Ga), tin (Sn), terbium (Tb) and any combination thereof; and D is selected from lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), ebium (Er), thulium (Tm), ytterbium (Yb), lutetium (Lu), scandium (Sc), titanium (Ti), vanadium (V), chromium (Cr), manganese (Mn), ferrum (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), hafnium (Hf), tantalum (Ta), tungsten (W), rhenium (Re), osmium (Os), iridium (Ir), platinum (Pt), gold (Au), gallium (Ga), indium (In), tin (Sn), antimony (Sb) and any combination thereof.

In some embodiments, A is selected from strontium (Sr) and barium (Ba). C is selected from cerium (Ce), zirconium (Zr), and manganese (Mn). D is selected from cerium (Ce) and yttrium (Y).

In some embodiments, the perovskite material is selected from $SrCeO_3$, $SrZr_{0.3}Ce_{0.7}O_3$, $BaMnO_3$, $BaCeO_3$, $BaZr_{0.3}Ce_{0.7}O_3$, $BaZr_{0.3}Ce_{0.5}Y_{0.2}O_3$, $BaZr_{0.1}Ce_{0.7}Y_{0.2}O_3$, $BaZrO_3$, $BaZr_{0.7}Ce_{0.3}O_3$, $BaCe_{0.5}Zr_{0.5}O_3$, $BaCe_{0.9}Y_{0.1}O_3$, $BaCe_{0.85}Y_{0.15}O_3$, and $BaCe_{0.8}Y_{0.2}O_3$. For example, for $SrCeO_3$, A is Sr, C is Ce, $a=1$, $b=0$, $c=1$, $d=0$, and $\delta=0$. For $SrZr_{0.3}Ce_{0.7}O_3$, A is Sr, C is Zr, D is Ce, $a=1$, $b=0$, $c=0.3$, $d=0.7$, and $\delta=0$. For $BaMnO_3$, A is Ba, C is Mn, $a=1$, $b=0$, $c=1$, $d=0$, and $\delta=0$. For $BaCeO_3$, A is Ba, C is Ce, $a=1$, $b=0$, $c=1$, $d=0$, and $\delta=0$. For $BaZr_{0.3}Ce_{0.7}O_3$, A is Ba, C is Zr, D is Ce, $a=1$, $b=0$, $c=0.3$, $d=0.7$, and $\delta=0$. For $BaZr_{0.3}Ce_{0.5}Y_{0.2}O_3$, A is Ba, C is Zr, D is combination of Ce and Y, $a=1$, $b=0$, $c=0.3$, $d=0.7$, and $\delta=0$. As one of ordinary skill in the art can understand from the above, more examples are omitted here to avoid obscuring the disclosure in unnecessary details.

In some embodiments, the method is operated at a temperature in a range from about 700° C. to about 870° C., a weight ratio of steam to hydrocarbon is in a range from about 3:7 to about 7:3, and the hydrocarbon comprises at least one of ethane, heptane, liquid petroleum gas, naphtha, and gas oil.

In some embodiments, the method is operated at a temperature in a range from about 480° C. to about 600° C., wherein the hydrocarbon comprises bottoms from atmospheric and vacuum distillation of crude oil and the mixture comprises from about 1 wt % to about 2 wt % steam.

In some embodiments, the perovskite material is $SrZr_{0.3}Ce_{0.2}O_3$.

In some embodiments, the perovskite material is $BaZr_{0.3}Ce_{0.2}O_3$.

In some embodiments, the perovskite material is $BaZr_{0.1}Ce_{0.7}Y_{0.2}O_3$.

In some embodiments, the perovskite material is $BaCe_{0.8}Y_{0.2}O_3$.

The perovskite material may be a coating applied using different methods, for example, air plasma spray, slurry coating, sol-gel coating, and solution coating. In some embodiments, the perovskite material is coated using air plasma spray method.

The reactor may be any reactor in which hydrocarbon is cracked. In some embodiments, the reactor comprises at least one of a furnace tube, a tube fitting, a reaction vessel, and a radiant tube.

DEFINITIONS

As used herein, the term "reactor" refers to but is not limited to at least one of a furnace tube, a tube fitting, a reaction vessel, and a radiant tube, used in petrochemical processes.

As used herein the term "cracking hydrocarbon" refers to but is not limited to processes in which hydrocarbons such as ethane, propane, butane and naphtha are cracked in reactors, in the presence of from about 30 to 70 weight percentage of steam, at temperatures of from about 700° C. to 870° C. in order to produce light olefins such as ethylene and propylene. Sometimes, hydrocarbons such as bottoms from atmospheric and vacuum distillation of crude oil are cracked in reactors at a temperature in a range from about 480 to about 600° C. in the presence of about 1 wt % to about 2 wt % steam.

As used herein the term "coke" refers to but is not limited to carbonaceous solid or liquid or particulates or macromolecules forming the carbonaceous solid or liquid, which are derived from coal, petroleum, wood, hydrocarbons and other materials containing carbon and which include, for example, carbon black, tar, and pyrolytic coke existing in hydrocarbon cracking furnace.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

The following examples are included to provide additional guidance to those of ordinary skill in the art in practicing the claimed invention. Accordingly, these examples do not limit the invention as defined in the appended claims.

A lab scale hydrocarbon-cracking furnace was built up. Due to structure similarity of naphtha, heptane was used as the source of hydrocarbon.

Samples on quartz sample holders were placed at the constant temperature region of the cracking furnace. The furnace door was then closed. Argon gas was fed in the furnace at the flow rate of 100 standard cubic centimeter per minute (sccm). The cracking furnace was heated to 880° C. with the ramping rate of 20° C./min. A vaporizer was heated to 350° C. within 30 minutes.

When the temperature of the cracking furnace reached 880° C. and the temperature of the vaporizer reached 350° C., water was pumped using a piston pump into the vaporizer with the flow rate of 1.58 ml/min. Argon gas feeding was stopped. After 5 minutes, heptane was pumped using a piston pump into the vaporizer with the flow rate of 2.32 ml/min to be vaporized and mixed with the steam in the vaporizer in a 1:1 weight ratio. The temperature of the cracking furnace was maintained at desired temperature, e.g., 800+/−5° C. or 860+/−5° C. for desired time before stopping the pumpings of the heptane and water. The residence time of the heptane and steam in the cracking furnace was 1.5 seconds, unless otherwise specified. Argon gas was fed again at the flow rate of 100 sccm before the cracking furnace and the vaporizer were shut down. When the cracking furnace cooled down, argon gas feed was stopped and the furnace door was opened to take out the sample holders.

Comparative Example

Square pellets each with the dimension of 6×6×1 mm³ made of materials commonly used in hydrocarbon-cracking reactors, i.e., 310S, incoloy 800HT, incoloy 825, $Al_2O_3$, $SiN_x$, SiC and $SiO_2$ were used as samples. Compositions of the alloy pellets, i.e., 310S, incoloy 800HT, and incoloy 825 are shown in table 1 below. Electric balance was used to measure the weight of each pellet before and after cracking experiment. Weights of cokes deposited on the pellets changed with time and are shown in table 2 below.

TABLE 2

| time (hour(s)) | 310S (g) | incoloy 800HT (g) | incoloy 825 (g) | $Al_2O_3$ (g) | $SiN_x$ (g) | SiC (g) | $SiO_2$ (g) |
|---|---|---|---|---|---|---|---|
| 0 | 0.00 | 0.00 | 0.00 | 0.00 | 0.00 | 0.00 | 0.00 |
| 2 | 0.23 | 0.35 | 0.29 | | | | |
| 2.5 | | | | 0.17 | 0.18 | 0.16 | 0.17 |
| 4 | 0.38 | 0.50 | 0.45 | | | | |
| 4.5 | | | | 0.31 | 0.34 | 0.30 | 0.29 |
| 6 | 0.59 | 0.74 | 0.80 | | | | |
| 8 | 0.81 | 0.98 | 0.75 | 0.56 | 0.58 | 0.62 | |
| 10 | 0.90 | 1.05 | 0.97 | 0.65 | 0.77 | 0.70 | |

Example 1

The perovskite materials were prepared by solid state reaction method. Using $BaZr_{0.3}Ce_{0.5}Y_{0.2}O_3$ as an example, stoichiometric amounts of high-purity barium carbonate, zirconium oxide, cerium oxide, and yttrium oxide powders (all from sinopharm chemical reagent Co., Ltd. (SCRC), Shanghai, China) were mixed in ethanol and ball-milled for 12 hours. The resultant mixtures were then dried and calcined at 1100° C. in air for 6 hours to form the perovskite powder. The powder was iso-statically pressed at 274.6 MPa for 10 minutes to become a disk. The disk was then sintered at 1400° C. for 6 hours in air. The sintered disk was polished to have a thickness of 1 mm. The perovskite phase was confirmed using an X-ray diffractometer (D8 Advance, Bruker AXS GmbH, Karlsruhe, Germany).

Example 2

Disks made from $SrCeO_3$, $SrZr_{0.7}Ce_{0.7}O_3$, $BaMnO_3$, $BaCeO_3$, $BaZr_{0.3}Ce_{0.7}O_3$, and $Al_2O_3$ and having a thickness of 1 mm and a diameter of 10 mm were used as samples and stayed in the cracking furnace at 800° C.+/−5° C. for 2 hours. No coke depositions were observed on surfaces of the $SrCeO_3$ disk, the $SrZr_{0.3}Ce_{0.7}O_3$ disk, the $BaMnO_3$ disk, the $BaCeO_3$ disk, and the $BaZr_{0.3}Ce_{0.7}O_3$ disk while the coke deposition was observed on the $Al_2O_3$ disk.

The X-ray Diffraction (XRD) results of the $BaZr_{0.3}Ce_{0.7}O_3$ disk before and after the experiment demonstrate that this material is rather stable in the experiment.

Example 3

Disks of 1 mm thick and 10 mm diameter made from $BaCO_3$, $BaTiO_3$, the mixture of $CeO_2$ and $BaCO_3$, and $Al_2O_3$, respectively, were used as samples and stayed in the cracking furnace at 800° C. for 2 hours. It was found that small amount of coke appeared on the surface of $BaCO_3$ disk, relatively more cokes were deposited on the $BaTiO_3$ and $Al_2O_3$ disks, and no coke was deposited on the $CeO_2$ and $BaCO_3$ mixture disk. XRD characterization shows that the perovskite material $BaCeO_3$ was formed from the $CeO_2$ and $BaCO_3$ mixture in-situ during the experiment. It suggests

TABLE 1

| | Cr (wt %) | Ni (wt %) | Fe (wt %) | Mn (wt %) | Si (wt %) | S (wt %) | P (wt %) | Cu (wt %) | Mo (wt %) | Al (wt %) | Ti (wt %) | C (wt %) |
|---|---|---|---|---|---|---|---|---|---|---|---|---|
| 310S | 25.6 | 18.9 | 52 | 1.6 | 0.4 | — | — | — | — | — | — | 1.5 |
| Incoloy 800HT | 20.62 | 30.76 | 45.57 | 0.89 | 0.65 | 0.005 | — | 0.29 | — | 0.57 | 0.56 | 0.082 |
| Incoloy 825 | 20.80 | 41.07 | 31.22 | 0.51 | 0.32 | 0.003 | 0.020 | 2.02 | 2.95 | 0.20 | 0.89 | 0.015 | that the perovskite material $BaCeO_3$ with Ba on A site and Ce on C site has higher anti-coking performance than $BaCO_3$, $BaTiO_3$ and $Al_2O_3$.

Example 4

A coupon made from alloy 310S with the dimension of 10×30×1 $mm^3$ was used as the substrate. Before coating, the substrate was cleaned carefully as follows: ultrasonic agitation in acetone and ethanol for 30 minutes, respectively, to remove organic contaminants, ultrasonic agitation in HCl (3.3 wt %) aqueous solution for 30 minutes to etch the substrate surface, ultrasonically rinsing in DI-water, and finally dried completely by compressed air. After ball milling and granulation process to make the average size of $BaZr_{0.1}Ce_{0.7}Y_{0.2}O_3$ powders to be around 20 micrometers, the powders were fed in an air plasma spray system to deposit $BaZr_{0.1}Ce_{0.7}Y_{0.2}O_3$ coating on the fully cleaned 310S substrate. XRD results identified the perovskite phase of $BaCe_{0.7}Zr_{0.1}Y_{0.2}O_3$ in the coating.

Example 5

The coated alloy coupon obtained in example 4 was then used as a sample and stayed in the cracking furnace at 860° C. for 8 hours in the heptane/steam (1:1 wt) mixture. It was observed that no coke was formed on the $BaZr_{0.1}Ce_{0.7}Y_{0.2}O_3$ film. Energy disperse spectroscopy (EDS) analysis was performed after the experiment and confirmed that no carbon can be identified on the surface of the $BaZr_{0.1}Ce_{0.7}Y_{0.2}O_3$ film. However, black carbon was observed on the blank section of the alloy substrate without the $BaZr_{0.1}Ce_{0.7}Y_{0.2}O_3$ film. This experiment suggests that the $BaZr_{0.1}Ce_{0.7}Y_{0.2}O_3$ film is effective for anti-coking.

Example 6

Sample 1 (the mixture of carbon black and $BaZr_{0.3}Ce_{0.7}O_3$ powders with a weight ratio of 1:10, total weight: 330 mg) and sample 2 (the carbon black powder, 30 mg) were tested in 50:50 (vol) helium:steam mixture using a thermogravimetric analyzer (TGA) (TG 151, from Calm Instruments, Inc., Cerritos, Calif., USA). The heating rate of TGA was 5° C./min, and the temperature range was 400° C. to 950° C. The weights of the samples were measured at different temperatures. The weight reduction percentages of carbon black in the samples were calculated out and shown in FIG. 1. Nicolet™ 380 FT-IR spectrometer from Thermo Electron Scientific Instruments Corp., Madison, Wis. USA was used to analyze the concentration of generated carbon dioxide at different temperatures. The concentrations of carbon dioxide at different temperatures are shown in FIG. 2.

FIG. 1 shows that more carbon black was consumed in the sample 1 than in the sample 2, especially when the temperature is around and higher than 800° C. FIG. 2 shows that more carbon dioxide were generated from the sample 1 than from the sample 2. The experiment suggests that the $BaZr_{0.3}Ce_{0.7}O_3$ may be used in the temperature range of 400° C. to 950° C. where coke formation/existence is not desired.

Example 7

Samples 3-13 were tested in 50:50 (vol) helium:steam mixture by using TGA. Samples 3-5 and 7-13 are powder mixtures of carbon black with $BaZr_{0.3}Ce_{0.7}O_3$, $BaCeO_3$, $BaCe_{0.5}Zr_{0.5}O_3$, $BaZr_{0.7}Ce_{0.3}O_3$, $BaZrO_3$, $BaZr_{0.1}Ce_{0.7}Y_{0.2}O_3$, $BaCe_{0.85}Y_{0.15}O_3$, $BaCO_3$, $BaCe_{0.9}Y_{0.1}O_3$, and $BaCe_{0.8}Y_{0.2}O_3$ respectively (weight ratio of 1:10, total weight: 330 mg). Sample 6 was carbon black powder (30 mg). The heating rate of TGA was 5° C./min, and the temperature range was from about 400° C. to about 950° C. The weight reduction percentages of carbon black in the samples were calculated out and shown in FIG. 3.

FIG. 3 shows more carbon black was consumed in the samples 3-5 and 7-13 than in the sample 6, especially when the temperature is around and higher than 785° C. It suggests that $BaZr_{0.3}Ce_{0.7}O_3$, $BaCeO_3$, $BaCe_{0.5}Zr_{0.5}O_3$, $BaZr_{0.3}Ce_{0.7}O_3$, $BaZrO_3$, $BaZr_{0.1}Ce_{0.7}Y_{0.2}O_3$, $BaCe_{0.85}Y_{0.15}O_3$, $BaCO_3$, $BaCe_{0.9}Y_{0.1}O_3$ and $BaCe_{0.8}Y_{0.2}O_3$ may be used in the temperature range of 400° C. to 950° C. where the coke formation/existence is not desired.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of inhibiting coke deposit formation in a hydrocarbon cracking reactor having an inner surface accessible to said hydrocarbon and wherein a hydrocarbon comprising ethane is cracked in the presence of steam at a temperature of about 480° C. to about 870° C. to form ethylene, said inner surface comprising a perovskite material selected from the group consisting of $BaZr_{0.3}Ce_{0.7}O_3$, $BaZr_{0.7}Ce_{0.3}O_3$, and $BaCe_{0.5}Zr_{0.5}O_3$ and combinations thereof whereby said perovskite gasifies said coke to produce CO, $CO_2$, and hydrogen.

2. A method as recited in claim 1 wherein said perovskite material is applied to said interior surfaces as a coating.

3. A method as recited in claim 1 wherein said perovskite material is present in the form of a pressed powder.

4. A method as recited in claim 1 wherein said inner surface is devoid of Ni.

5. A method as recited in claim 1 wherein the perovskite material is $BaZr_{0.7}Ce_{0.3}O_3$.

6. A method as recited in claim 1 wherein the perovskite material is $BaCe_{0.5}Zr_{0.5}O_3$.

7. The method of claim 1, being operated at a temperature in a range from about 700° C. to about 870° C. and wherein a weight ratio of steam to hydrocarbon is in a range from about 3:7 to about 7:3.

8. The method of claim 1, being operated at a temperature in a range from about 480 to about 600° C., and a weight percentage of the steam in the steam and hydrocarbon is about 1 wt % to about 2 wt %.

9. The method of claim 1, wherein the perovskite material is $BaZr_{0.3}Ce_{0.7}O_3$.

* * * * *

UNITED STATES PATENT AND TRADEMARK OFFICE
CERTIFICATE OF CORRECTION

PATENT NO. : 9,499,747 B2
APPLICATION NO. : 13/115610
DATED : November 22, 2016
INVENTOR(S) : Wang et al.

Page 1 of 2

It is certified that error appears in the above-identified patent and that said Letters Patent is hereby corrected as shown below:

On the Title Page

In item (57), under "ABSTRACT", in Column 2, Line 14, delete "ebium," and insert -- erbium, --, therefor.

In the Specification

In Column 2, Line 10, delete "ebium" and insert -- erbium --, therefor.

In Column 2, Line 35, delete "ebium" and insert -- erbium --, therefor.

In Column 3, Line 16, delete "ebium" and insert -- erbium --, therefor.

In Column 3, Line 43, delete "ebium" and insert -- erbium --, therefor.

In Column 3, Line 66, delete "8=0." and insert -- $\delta$=0. --, therefor.

In Column 4, Line 18, delete "$SrZr_{0.3}Ce_{0.2}O_3$." and insert -- $SrZr_{0.3}Ce_{0.7}O_3$. --, therefor.

In Column 4, Line 20, delete "BaZr0.3Ce0.2O3." and insert -- BaZr0.3Ce0.7O3. --, therefor.

In Column 7, Line 42, delete "Calm" and insert -- Cahn --, therefor.

In Column 7, Line 57, delete "were" and insert -- was --, therefor.

In Column 8, Line 19, delete "$BaZr_{0.3}Ce_{0.7}O_3$," and insert -- $BaZr_{0.7}Ce_{0.3}O_3$, --, therefor.

Signed and Sealed this
Second Day of May, 2017

Michelle K. Lee
*Director of the United States Patent and Trademark Office*

CERTIFICATE OF CORRECTION (continued)
U.S. Pat. No. 9,499,747 B2

In the Claims

In Column 8, Line 41, in Claim 2, delete "A method" and insert -- The method --, therefor.

In Column 8, Line 43, in Claim 3, delete "A method" and insert -- The method --, therefor.

In Column 8, Line 45, in Claim 4, delete "A method" and insert -- The method --, therefor.

In Column 8, Line 47, in Claim 5, delete "A method" and insert -- The method --, therefor.

In Column 8, Line 49, in Claim 6, delete "A method" and insert -- The method --, therefor.